(12) United States Patent
Rao et al.

(10) Patent No.: US 8,178,712 B2
(45) Date of Patent: May 15, 2012

(54) PROCESS FOR THE SYNTHESIS OF IBANDRONATE SODIUM

(75) Inventors: Dharamaraj Ramchandra Rao, Mumbai (IN); Rajendra Narayanrao Kankan, Mumbai (IN); Maruti Ganpati Ghagare, Mumbai (IN)

(73) Assignee: Cipla Ltd., Mumbai (IN)

( * ) Notice: Subject to any disclaimer, the term of this patent is extended or adjusted under 35 U.S.C. 154(b) by 538 days.

(21) Appl. No.: 12/303,918

(22) PCT Filed: Jun. 22, 2007

(86) PCT No.: PCT/IN2007/000255
§ 371 (c)(1),
(2), (4) Date: Dec. 8, 2008

(87) PCT Pub. No.: WO2008/035367
PCT Pub. Date: Mar. 27, 2008

(65) Prior Publication Data
US 2010/0228052 A1    Sep. 9, 2010

(30) Foreign Application Priority Data

Jun. 23, 2006 (IN) ............................ 994/MUM/2006

(51) Int. Cl.
C07F 9/38 (2006.01)
C07F 9/28 (2006.01)
A61K 31/66 (2006.01)
(52) U.S. Cl. .......... 558/158; 562/13; 562/553; 514/108; 564/15

(58) Field of Classification Search ........................ None
See application file for complete search history.

(56) References Cited

U.S. PATENT DOCUMENTS
4,927,814 A    5/1990    Gall et al.

FOREIGN PATENT DOCUMENTS
| WO | WO 2005/044831 A2 | 5/2005 |
| WO | WO 2005/063779 A2 | 7/2005 |
| WO | WO 2006/002348 A2 | 1/2006 |
| WO | WO 2006/045578 A2 | 5/2006 |

OTHER PUBLICATIONS

Bauss et al., "BM 21.0955, Monosodium salt, monohydrate. Bisphosphonate bone resorption inhibitor," *Drugs of the Future* (1994) 19 (1): 13-16.

Synthline References, "Ibandronic acid monosodium salt monohydrate, Ibandronate sodium hydrate, R-484, Ro-200-5450, BM-21.0955 monosodium salt monohydrate, RPR-102289A, CT-064, Bondronat, Bonviva (former Brand Name), Destara, Boniva, Bondenza," *Prous Science* (2004).

Form PCT/IPEA/409 completed on Nov. 14, 2008 for International Application PCT/IN2007/000255.

Wang et al., "Nonracemic betti base as a new chiral auxiliary: Application to total syntheses of enantiopure (2S,6R)-Dihydropinidine and (2S,6R)-Isosolenopsins." *J. Org. Chem* vol. 70. (2005).1897-1900.

Kurosu et al., "Efficient synthesis of tertiary amines from secondary amines." *Tetrahedron Letters* vol. 47 (2006).

*Primary Examiner* — Yate K Cutliff
(74) *Attorney, Agent, or Firm* — Merchant & Gould P.C.

(57) ABSTRACT

The present invention relates to an improved process for the synthesis of Ibandronate sodium of formula (I). The present invention also provides novel processes for the synthesis of 3-[N-(methylpentyl)amino]propionic acid (III).

24 Claims, No Drawings

PROCESS FOR THE SYNTHESIS OF IBANDRONATE SODIUM

This application is a National Stage Application of PCT/IN2007/000255, filed Jun. 22, 2007, which claims benefit of Serial No. 994/MUM/2006, filed Jun. 23, 2006 in India and which application(s) are incorporated herein by reference. To the extent appropriate, a claim of priority is made to each of the above disclosed applications.

FIELD OF INVENTION

The present invention relates to an improved process for the synthesis of Ibandronate sodium.

Further the present invention relates to novel processes for the synthesis of 3-[N-(methylpentyl)amino]propionic acid (III).

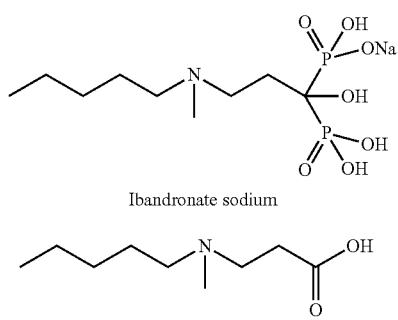

BACKGROUND OF THE INVENTION

Polyphosphonic acids and their pharmaceutical acceptable salts have been known for use in the treatment of diseases of bone and calcium metabolism. Several methods for making bisphosphonates have been described in the literature, for example Pamidronic acid, Alendronic acid, Risedronic acid and Zoledronic acid. These compounds have very less solubility in water, and hence can be easily isolated from the water. Whereas Ibandronic acid is easily soluble in water, as a result its isolation from water is very difficult.

U.S. Pat. No. 4,927,814 describes the process to make analogues of Ibandronic acid which involves the use of chlorobenzene, phosphorous acid and phosphorous trichloride and finally the Ibandronic acid is isolated by using Ion exchange resin chromatography, employing Amberlite IR-120 H+ column and eluted with water where elution is monitored electrophoretically. However these operations are very difficult and time consuming on an industrial scale. This patent claims broadly Ibandronate sodium but there is no exemplary disclosure for making Ibandronate sodium.

WO2005/044831 describes the process to make analogues of Ibandronic acid by using sulfolane as a solvent instead of chlorobenzene and isolating the acids from water. While the technique described for the isolation can be used for Pamidronic acid, Alendronic acid, Risedronic acid, and Zoledronic acid, this process cannot be used for isolating Ibandronic acid because of its high solubility in water.

WO2005/063779 describes the process to make Risedronic acid by adding acetone to the aqueous solution of Risedronic acid, and then isolating the acid. However this process also works well for Pamidronic acid, Alendronic acid, Risedronic acid, and Zoledronic acid even without addition of acetone, but the same process does not work for Ibandronic acid because of its high solubility in water.

Ibandronic acid being highly soluble in water does not precipitate out even after addition of solvent.

In the prior art processes, bisphosphonic acids like zoledronic acid, pamidronic acid, alendronic acid, risedronic acid etc. have been prepared by the reaction of corresponding carbonyl compounds (FIG. 1) with phosphorous acid, phosphorous halides, (example: phosphorous trichloride, phosphorous oxychloride, or phosphorous pentachloride) and then quenching the reaction mixture with water, heating the reaction mass to get bisphosphonic acid which is isolated and converted to the sodium salt of respective acid.

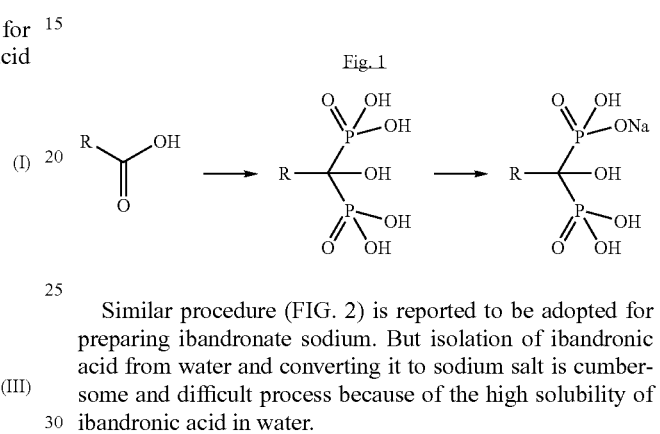

Similar procedure (FIG. 2) is reported to be adopted for preparing ibandronate sodium. But isolation of ibandronic acid from water and converting it to sodium salt is cumbersome and difficult process because of the high solubility of ibandronic acid in water.

The prior art further discloses various methods for the synthesis of compound (III), which is the key intermediate in the synthesis of Ibandronate sodium. U.S. Pat. No. 4,927,814, Drugs of Future 1994, 19(1), 13-16 describes a process wherein N-methyl pentyl amine is reacted with methyl acrylate to give the corresponding methyl ester which is further hydrolyzed to get compound (III).

Initially various attempts were made to synthesize the intermediate III. Scheme II shows two new alternate schemes for the synthesis of III which employs the use of methyl acrylate.

The processes described in the prior art involves the use of methyl acrylate, which is very obnoxious reagent, polymerizes on storage and needs to be distilled before using. This reagent is toxic, unstable; hence it is not preferred to be used on an industrial scale.

Further efforts were made for the synthesis of III which avoids the use of methyl acrylate, this was achieved by using methyl 3-bromopropionate as shown in Scheme I.

Therefore there is need for a simple, economical and industrially viable process for the synthesis of Ibandronate sodium.

The present invention provides a simple process for the synthesis of ibandronate sodium and its intermediate 3-[N-(methylpentyl)amino]propionic acid (III).

OBJECT OF INVENTION

Thus it is an object of the present invention to provide an improved process for the synthesis of Ibandronate sodium.

It is a further object of the present invention to provide an improved process for the synthesis of ibandronate sodium without the isolation of ibandronic acid.

Another object of the present invention provides an alternate process for the synthesis of the key intermediate (III).

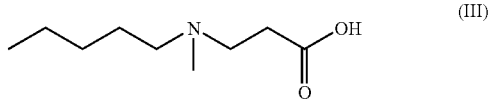
(III)

Yet another object of the present invention is to provide novel processes for the preparation of the key intermediate (III) from methyl acrylate.

SUMMARY OF INVENTION

According to one aspect of the present invention there is provided an improved process for the synthesis of Ibandronate sodium of formula (I) without the isolation of ibandronic acid comprising the steps of (FIG. 2)
  (i) Reaction of 3-[N-(methylpentyl)amino]propionic acid (III) with phosphorus acid, halophosphorus compound in an organic solvent at a temperature of 50° C. to 100° C.
  (ii) Solvent removal followed by reflux in water and addition of sodium hydroxide.
  (iii) Precipitation of ibandronate sodium of formula (I) in an organic solvent.

According to another aspect of the invention there is provided a novel process for the synthesis of 3-[N-(methylpentyl)amino]propionic acid (III) comprising the steps of (Scheme I),
  a) Condensation of N-methylbenzylamine with 1-bromopentane in the presence of a base.
  b) Debenzylation of N-methyl, N-pentyl benzyl amine (VI).
  c) Condensation of N-methyl, N-pentyl amine (V) with methyl-3-halopropionate in a solvent to give 3-[N-(methylpentyl)amino]propionate (IV).
  d) Hydrolysis of compound (IV).

According to yet another aspect of the invention there is provided an alternate process for the synthesis of 3-[N-(methylpentyl)amino]propionic acid (III) comprising the steps of,
  a) Condensation of N-methyl benzyl amine with 1-bromo pentane in presence of a base and solvent.
  b) Debenzylation of N-methyl N-pentyl benzyl amine.
  c) Condensation of N-methyl pentyl amine with methyl acrylate in toluene.
  d) Hydrolysis of 3-[N-(methylpentyl)amino]propionate.

According to yet another aspect of the invention there is provided an alternate process to prepare 3-[N-(methylpentyl)amino]propionic acid (III) comprising the steps of
  a) Condensation of N-methyl benzyl amine with methyl acrylate in presence of a base.
  b) Debenzylation of 3[N-(methyl benzyl)]propionate.
  c) Condensation of 3-N-methyl propionate with bromopentane.
  d) Hydrolysis 3-[N-(methylpentyl)amino]propionate to get intermediate (III).

DETAILED DESCRIPTION

In the prior art processes, the bisphosphonic acids have been prepared by the reaction of respective carbonyl compounds with phosphorous acid, phosphorous halides and then quenching the reaction mixture with water, heating the reaction mass to get bisphosphonic acid, which is isolated and converted, to the sodium salt. But isolation of ibandronic acid from water and converting it to sodium salt is cumbersome and difficult process because of the high solubility of ibandronic acid in water.

The present inventors have provided an improved process for the preparation of Ibandronate sodium in an organic solvent without isolating the ibandronic acid.

The prior art further discloses various methods for the synthesis of compound (III), which is the key intermediate in the synthesis of Ibandronate sodium using methyl acrylate as a raw material.

The present inventors have provided novel processes for the synthesis of the key intermediate (III).

The present invention provides a process for the synthesis of ibandronate sodium (I) from 3-[N-(methylpentyl)amino] propionic acid (III) wherein compound (III) is reacted with phosphorous acid, phosphorous trichloride or $POCl_3$, or $PCl_5$ in an organic solvent like toluene, chlorobenzene, xylene, methane sulphonic acid, benzene sulphonic acid, ethylene dichloride, tetrahydrofuran, tetrachloro ethane, dioxane preferably toluene at a temperature ranging from 50 to 100° C. preferably at 85-90° C. for 8-10 hrs. The reaction mass is cooled to 25-30° C. The solvent is removed by distillation under vacuum at about 40° C. Water is added to the residue and refluxed for 10 hrs and later concentrated to half. The pH of the concentrate is adjusted to 4.3-4.5 with dilute NaOH solution. The reaction mass is concentrated to residue. Methanol is added dropwise to the residue under stirring and the resulting solid is filtered. The solid is dissolved in water and precipitated with C1 to C4 alcohols, C3 to C7 ketones or esters, DMSO, acetonitrile, tetrahydrofuran, C5 to C7 acyclic/cyclic saturated hydrocarbons, dioxane preferably methanol and the filtered solid is slurried in a ketonic solvent like acetone, methyl isobutyl ketone, methyl ethyl ketone preferably acetone to get pure Ibandronate sodium.

The present invention also provides a process for the synthesis of 3-[N-(methylpentyl)amino]propionic acid (III) wherein N-methylbenzylamine is reacted with 1-bromo pentane in presence of a base like potassium carbonate, sodium carbonate, sodium bicarbonate, potassium bicarbonate preferably potassium carbonate to get N-methyl, N-pentyl benzyl amine (VI) which is subjected to debenzylation using 10% Pd/C as catalyst in an alcoholic solvent to get N-methyl, N-pentylamine (V) which is isolated in pure form as an acid addition salt of an organic acid such as fumaric acid, citric acid, maleic acid, edetic acid preferably it is isolated as an oxalate salt. Compound (V) is reacted with methyl-3-halopropionate like methyl 3-chloro propionate, methyl-3-bromo propionate, methyl 3-iodo propionate more preferably methyl-3-bromo propionate in a suitable solvent preferably toluene in the presence of a base preferably potassium carbonate at a temperature ranging from 25° C. to 80° C. preferably at 70° C. to get 3-[N-(methylpentyl)amino]propionate (IV), which is further hydrolyzed to give 3-[N-(methylpentyl) amino]propionic acid hydrochloride (III) which is the key intermediate for the synthesis of Ibandronate sodium.

The present invention provides an alternate process for the synthesis of 3-[N-(methylpentyl)amino]propionic acid (III) wherein N-methyl benzyl amine is condensed with 1-bromo pentane in presence of potassium carbonate, using acetone as solvent to give N-methyl N-pentyl benzyl amine. This is debenzylated using palladium on carbon as catalyst and alcohol as solvent. The resulting product N-methyl pentyl amine is condensed with methyl acrylate in toluene to get 3-[N-(methylpentyl)amino]propionate, which is further hydrolysed to obtain Intermediate III.

The present invention further provides an alternate process for the synthesis of 3-[N-(methylpentyl)amino]propionic acid (III) wherein N-methyl benzyl amine is condensed with methyl acrylate in presence of potassium carbonate to obtain 3[N-(methylbenzyl)]amino propionate. This is further debenzylated using palladium/C as catalyst to obtain 3-N-methyl amino propionate. This is condensed with 1-bromo pentane to obtain 3-[N-(methylpentyl)amino]propionate, which is further hydrolysed to get intermediate (III).

The present invention is described in detail in Scheme I.

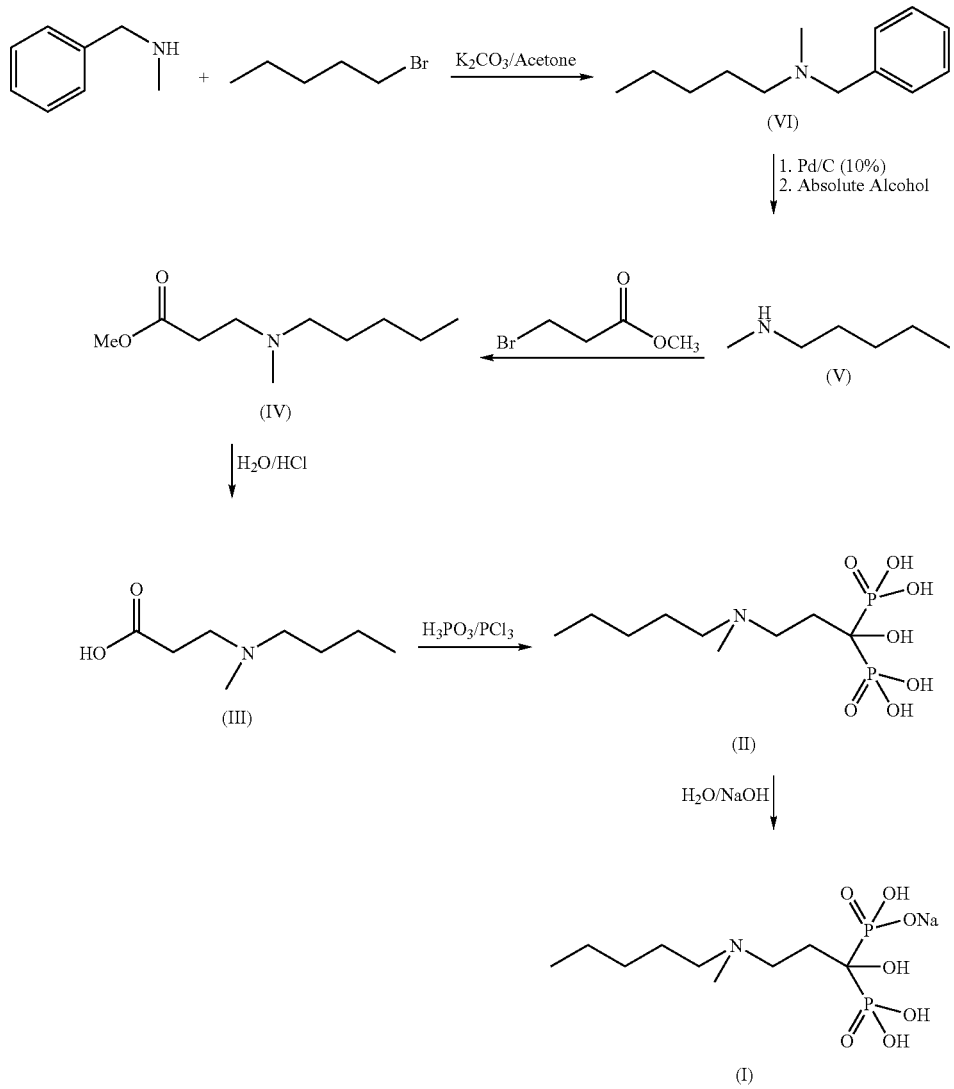

The alternate process for the preparation of the key intermediate (III) used for the synthesis of Ibandronate sodium is shown in Scheme II.

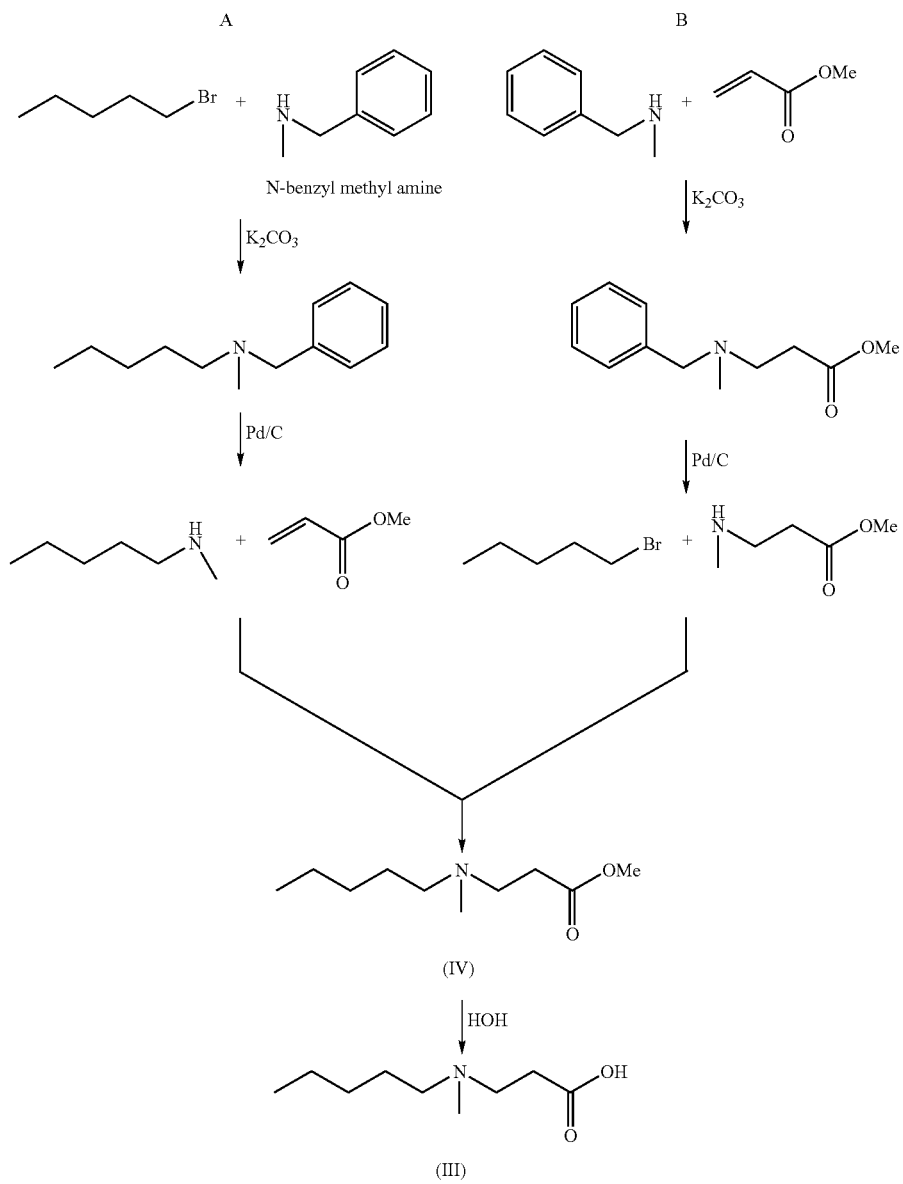

EXAMPLES

Preparation of N-Methyl N-Pentyl Benzyl Amine (VI)

N-methylbenzylamine 100 gms (0.82 moles), acetone (200 ml) and potassium carbonate 114 gms (0.82 moles) were mixed at room temperature and to the slurry obtained, 1-bromopentane 211.4 gms (1.4 moles) was added dropwise at room temperature. Reaction mixture was stirred at room temperature for 18 hours. The reaction mixture was filtered, washed with acetone and concentrated under vacuum to an oily residue. The residue was dissolved in MDC (200 ml) and washed with water (3×100 ml). Organic layer was dried over sodium sulphate and concentrated under vacuum to get 154 gms of the title compound as an oil.

Preparation of N-Methyl, N-Pentylamine (V) Oxalate

Debenzylation of N-methyl-N-pentylbenzylamine (154.8 gms, 0.81 moles), was carried out under a constant pressure of 2 kg/cm$^2$ of hydrogen, using 10% Pd/C as catalyst, and absolute alcohol (750 ml) as a solvent over a period of 12 hrs. The reaction mixture was filtered through hyflo. To the filtrate, oxalic acid (127 gms, 1.01 moles) was added and the mixture was stirred at room temperature for 1 hr, following which stirring was continued at 5-10° C. for 1 hr. The resulting salt was filtered and dried under vacuum for 24 hrs to obtain white solid (81 gms)

Preparation of 3-[N-(methylpentyl)amino]propionic acid hydrochloride (III)

N-methyl-N-pentylamine oxalate (81 gms) was dissolved in water (250 ml). Liquid ammonia was added dropwise to make pH basic (pH=12) and further extracted with methylene dichloride (2×400 ml). Combined organic layer was concentrated under vacuum to obtain N-methyl-N-pentylamine (59.06 gms), which was taken in toluene (590 ml), to which potassium carbonate (80.592 g, 0.584 moles) was added. To this white suspension methyl-3-bromopropionate (99.478 g, 0.595 moles) was added dropwise. The temperature of reaction mass was gradually increased to 70° C. and the reaction mass was stirred at this temperature for three hours. The reaction mass was filtered and the filtrate which contains 3-[N-(methylpentyl)amino]propionate was directly taken for hydrolysis. To the filtrate, water (350 ml) was added and toluene was distilled off. The reaction mass was refluxed for three hours, charcoalized and filtered. The pH of the filtrate was made acidic (pH=2) using Conc. HCl and it was further concentrated to residue which on stripping twice with acetone (150 ml) gave a white waxy solid, 3-[N-(methylpentyl) amino]propionic acid hydrochloride (75.12 g).

Preparation of Ibandronate Sodium (I)

A mixture of 3-[N-(methylpentyl)amino]propionic acid hydrochloride (75.12 gms, 0.358 moles), phosphorous acid (123.91 gms, 1.51 moles) and toluene (1500 ml) was heated to 70-75° C. Phosphorous trichloride (180.37 gms, 1.31 moles) was added dropwise over a period of 1.5 hrs. The reaction mass was heated to 80-85° C. and stirred at this temperature for 7-8 hours. Thereafter reaction mass was cooled to 25-30° C. and toluene was decanted. To the residue water (1500 ml) was added and refluxed for 10 hours, charcoalized, filtered through hyflo and concentrated to half its initial volume. The pH of the concentrate was adjusted to 4.3-4.5 with dilute sodium hydroxide. The reaction mass was concentrated to residue to which methanol (400 ml) was added dropwise and stirred for 1 hr. The resulting suspension was filtered. The filtered product was slurried in methanol (480 ml) and filtered. The solid obtained was further dissolved in water (500 ml). Methanol (500 ml) was added dropwise to the clear solution at 25-30° C. Solid obtained was stirred for 1 hour and filtered. Solid was slurried in 400 ml of acetone and filtered, dried under vacuum at 50° C. for 48 hrs to get 53.33 gms of Ibandronate sodium.

Preparation of 3-[(N-methylpentyl)amino]propionic acid hydrochloride (III) (Scheme II a)

a) Preparation of N-methyl N-pentyl benzylamine:
N-methylbenzylamine (50 g, 0.41 moles), acetone (100 ml) and potassium carbonate 57 g (0.41 moles) were mixed at room temperature and to the slurry obtained, 1-bromopentane 105.7 g (0.7 moles) was added dropwise at the room temperature. Reaction mixture was then stirred at room temperature for 18 hrs. The reaction mixture was filtered, washed with acetone and concentrated under vacuum to an oily residue. The residue was dissolved in 100 ml of MDC and washed with water (3×50 ml). Organic layer was dried over sodium sulphate and concentrated under vacuum to get N-methyl N-pentyl benzylamine as an oil. (Yield=77 g, 98%).

b) Preparation of N-methyl, N-pentylamine oxalate:
Debenzylation of N-methyl, N-pentylbenzylamine (77 g, 0.40 moles), was carried out under a constant pressure of 2 kg of hydrogen, over a period of 12 hrs, using 10% Pd/C as catalyst, and absolute alcohol (375 ml) as a solvent. The reaction mixture was filtered through hyflo. To the filtrate, oxalic acid (63.5 g, 0.505 moles) was added and the mixture was stirred at room temperature for 1 hr, following which stirring was continued at 5-10° C. for 1 hr. The obtained white mass was filtered out and dried under vacuum for 24 hrs to obtain white oxalate salt. (40.5 g, 52.32%)

c) Preparation of 3-[(N-methylpentyl)amino]propionic acid hydrochloride
N-methyl-N-pentylamine oxalate (40.5 g, 0.212 moles) was dissolved in 125 ml of water, liquid ammonia was added dropwise to make pH basic (pH=10-12) and then extracted with methylene, dichloride (2×200 ml). The combined organic layer was dried over anhydrous sodium sulfate and concentrated under vacuum to oil (29.53 g, 72.91%).

N-methyl-N-pentylamine (29.53 g, 0.292 moles), and 59 ml toluene was mixed. To this mixture freshly distilled methyl acrylate (25.11 g, 0.292 moles) was added dropwise. The reaction mixture was heated at 70-80° C. After three hours the reaction mass was cooled to 40° C. and 120 ml of water was added. Toluene was distilled off and the reaction mass was then refluxed for 3-4 hrs, charcoalised and filtered through hyflo. The pH of the reaction mass was adjusted to 2-3 with conc. hydrochloric acid and then acidic filtrate was concentrated under vacuum to obtain the oily residue which was stripped out with Acetone (2×75 ml) to obtain white solid (39.08 g, 75.56%)

Preparation of 3-[(N-methylpentyl)amino]propionic acid hydrochloride (III) (Scheme II B)

a. Preparation of 3-[N-(benzylmethyl)amino]propionate:
To a mixture of N-methylbenzylamine (40 g, 0.328 moles) and methanol (100 ml), obtained at room temperature, methyl acrylate (28.42 g, 0.328 moles) was added dropwise. The reaction mass was stirred at 65° C. for 45 min, cooled and concentrated under vacuum at 50° C. to obtain 3-[N-(benzylmethyl)amino]propionate, as an oil (Yield=58.82 g, 85.95%).

b. Preparation of 3-[N-(methyl)amino]propionate oxalate:
Debenzylation of 3-[N-(benzylmethyl)amino]propionate (58.82 g, 0.284 moles), was carried out under a constant pressure of 2 kg/cm$^2$ of hydrogen, over a period of 13 hrs, using 10% Pd/C as catalyst, and methanol (588 ml) as solvent. The reaction mixture was filtered through hyflo. To the filtrate, oxalic acid (89.75 g, 0.712 moles) was added and the mixture was stirred at room temperature for 1 hr, following which stirring was continued at 5-10° C. for 1 hr. The obtained white mass was filtered out and dried under vacuum at 50° C. for 24 hrs to obtain white oxalate salt (40.61 g, 58.82%).

c. Preparation of 3-[N-(methylpentyl)amino]propionic acid hydrochloride:
3-[N-(methyl)amino]propionate oxalate (40.61 g, 0.196 moles) was dissolved in 320 mL of distilled water, methylene dichloride (160 mL) was added and liquid ammonia was added dropwise to make pH basic (pH=10-12). The organic layer was separated and the aqueous layer was extracted with methylene dichloride (2×160 ml). The combined organic fraction was dried over anhydrous sodium sulfate and concentrated under vacuum to obtain 3-[N-(methyl)amino]propionate as an oil (27.16 g, 74%).

To a mixture of 3-[N-(methyl)amino]propionate (27.16 g, 0.144 moles), potassium carbonate (19.98 g, 0.144 moles), and acetone (268 mL), obtained at room temperature, n-bromopentane (37.18 g, 0.268 moles) was added dropwise and the reaction mixture was stirred at room temperature. After sixteen hours the reaction mixture was filtered and concentrated in vacuo to obtain pale yellow oily 3-[N-(methylpentyl) amino]propionate (Yield=42.42 g, 67.02%).

A mixture of 3-[N-(methylpentyl)amino]propionate (42.42 g, 0.224 moles) and water (120 mL) was refluxed for two hours, charcoalized and filtered through hyflo. The pH of the filtrate was adjusted to 2-3 with conc. hydrochloric acid and then the acidic filtrate was concentrated under vacuum to obtain a white solid of 3-[N-(methylpentyl)amino]propionic acid hydrochloride (17.66 g, 45.45%)

Preparation of 3-[N-(methylpentyl)amino]propionic acid hydrochloride (III)

N-methyl-N-pentylamine oxalate (75 gms) was taken in 750 ml of toluene. 107.5 gms of potassium carbonate (0.778 moles) was added and stirred to get white suspension. To this white suspension methyl-3-bromopropionate (87.52 g, 0.521 moles) was added dropwise. The temperature of reaction mass was gradually increased to 65-70° C. and the reaction mass was stirred at this temperature for three hours. The reaction mass was filtered hot and the filtrate containing 3-[N-(methylpentyl)amino]propionate was directly taken for hydrolysis. To the filtrate, water (920 ml) was added and toluene was distilled off. The reaction mass was refluxed for three hours, charcoalized and filtered. The pH of the filtrate was made acidic (pH=2) using Conc. HCl and it was further concentrated to residue which on stripping twice with acetone (1600 ml) gave a white waxy solid, 3-[N-(methylpentyl) amino]propionic acid hydrochloride (75 g).

The invention claimed is:

1. A process for the synthesis of Ibandronate sodium of formula (I) comprising:
    (i) N-alkylating N-benzyl methylamine with 1-bromopentane or methyl-3-halopropionate to form an N-alkylated intermediate;
    (ii) Debenzylating the N-alkylated intermediate to form a secondary amine;
    (iii) N-alkylating the secondary amine with 1-bromopentane or methyl-3-halopropionate to obtain methyl 3-[N-(methylpentyl)amino]propionate of formula (IV)

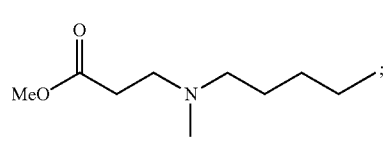

(IV)

(iv) Hydrolysing 3-[N-(methylpentyl)amino]propionate of formula (IV) to obtain methyl 3-[N-(methylpentyl) amino]propionic acid of formula III;

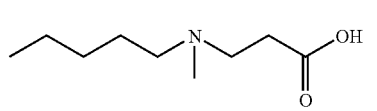

(III)

(v) Reaction of 3-[N-(methylpentyl)amino]propionic acid (III) with phosphorus acid, halophosphorus compound in an organic solvent selected from toluene, chlorobenzene, xylene, methane sulphonic acid benzene sulphonic acid, ethylene dichloride, tetrahydrofuran, tetrachloro ethane, dioxane, at a temperature of 50° C. to 100° C.;
    (vi) Solvent removal followed by reflux in water and addition of sodium hydroxide; and
    (vii) Precipitation of ibandronate sodium of formula (I) in an organic solvent without the isolation of ibandronic acid

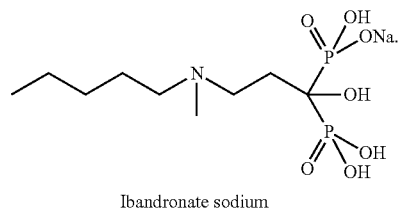

Ibandronate sodium

2. The process as claimed in claim 1 wherein the halophosphorus compound is selected from the group comprising of phosphorous trichloride, POCl$_3$, PCl$_5$.

3. The process as claimed in claim 1 wherein the organic solvent is toluene.

4. The process as claimed in claim 1 wherein the temperature range of step (i) is 85° C. to 90° C.

5. The process as claimed in claim 1 wherein the organic solvent for precipitation of ibandronate sodium of step (iii) is selected from the group consisting of C1 to C4 alcohols, C3 to C7 ketones or esters, DMSO, acetonitrile, tetrahydrofuran C5 to C7 acyclic/cyclic saturated hydrocarbons, and dioxane.

6. The process as claimed in claim 5 wherein the organic solvent for precipitation of ibandronate sodium is methanol.

7. The process for the synthesis of ibandronate sodium as claimed in claim 1, wherein synthesis of 3-[N-(methylpentyl) amino]propionic acid (III) comprises:
    (i) N-alkylating N-methylbenzylamine with 1-bromopentane in the presence of a base to obtain N-methyl, N-pentyl benzyl amine of formula (VI);

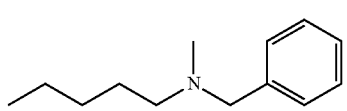

(VI)

(ii) Debenzylating N-methyl, N-pentyl benzyl amine of formula (VI) to obtain N-methyl, N-pentylamine of formula (V);

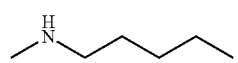

(V)

(iii) N-alkylating N-methyl, N-pentyl amine of formula (V) with methyl-3-halopropionate in a solvent at 25° C. to 80° C. to obtain methyl-3-[N-(methylpentyl)amino] propionate of formula (IV); and

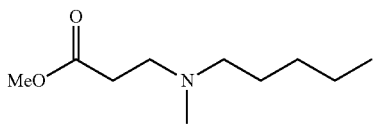

(iv) Hydrolysing methyl 3-[N-(methylpentyl)amino]propionate of formula (IV) to obtain 3-[N-(methylpentyl)amino]propionic acid of formula III

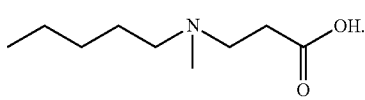

8. The process as claimed in claim 7 wherein the base of step (i) is selected from potassium carbonate, sodium carbonate, sodium bicarbonate, and potassium bicarbonate.

9. The process as claimed in claim 8 wherein the base is potassium carbonate.

10. The process as claimed in claim 7 wherein the catalyst of step (ii) for debenzylation is Palladium/C.

11. The process as claimed in claim 7 wherein the methyl-3-halopropionate of step (iii) is selected from methyl 3-chloro propionate, methyl-3-bromo propionate, and methyl 3-iodo propionate.

12. The process as claimed in claim 11 wherein the methyl-3-halopropionate is methyl-3-bromo propionate.

13. A process for preparing 3-[N-(methylpentyl)amino]propionic acid of formula III comprising:
(i) N-alkylating N-benzyl methylamine with 1-bromopentane or methyl-3-halopropionate to form an N-alkylated intermediate;
(ii) Debenzylating the N-alkylated intermediate to form a secondary amine;
(iii) N-alkylating the secondary amine with 1-bromopentane or methyl-3-halopropionate to obtain methyl 3-[N-(methylpentyl)amino]propionate of formula (IV)

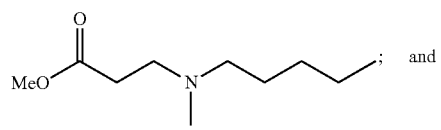

(iv) Hydrolysing 3-[N-(methylpentyl)amino]propionate of formula (IV) to obtain methyl 3-[N-(methylpentyl)amino]propionic acid of formula III

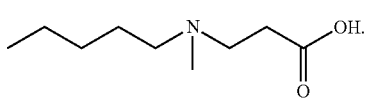

14. The process for preparing 3-[N-(methylpentyl)amino] propionic acid of formula III as claimed in claim 13 wherein the N-alkylated intermediate is N-methyl, N-pentyl benzyl amine or methyl 3-[N-(methylbenzyl)]amino propionate.

15. The process for preparing 3-[N-(methylpentyl)amino] propionic acid of formula III as claimed in claim 13 wherein the secondary amine is N-methyl, N-pentylamine or methyl 3-N-methyl amino propionate.

16. A process for preparing 3-[N-(methylpentyl)amino] propionic acid of formula III comprising:
(i) N-alkylating N-methylbenzylamine with 1-bromopentane in the presence of a base to obtain N-methyl, N-pentyl benzyl amine of formula (VI)

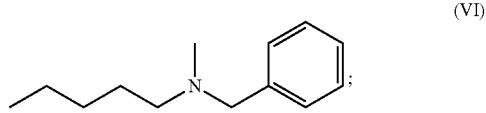

(ii) Debenzylating N-methyl, N-pentyl benzyl amine of formula (VI) to obtain N-methyl, N-pentylamine of formula (V)

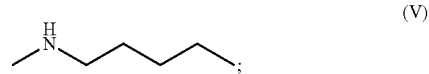

(iii) N-alkylating N-methyl, N-pentyl amine of formula (V) with methyl-3-halopropionate in a solvent at 25° C. to 80° C. to obtain methyl 3-[N-(methylpentyl)amino] propionate of formula (IV)

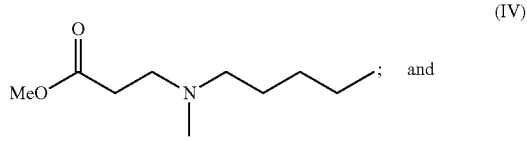

(iv) Hydrolysing 3-[N-(methylpentyl)amino]propionate of formula (IV) to obtain methyl 3-[N-(methylpentyl)amino]propionic acid of formula III

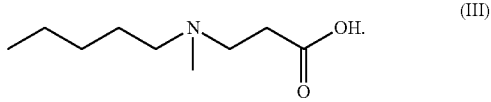

17. The process as claimed in claim 16 wherein the base is selected from the group comprising of sodium carbonate, sodium bicarbonate, potassium bicarbonate.

18. The process as claimed in claim 16 wherein the base is potassium carbonate.

19. The process as claimed in claim 16 wherein the catalyst for debenzylation is Palladium/C.

20. The process as claimed in claim 16 wherein the methyl-3-halopropionate is selected from the group comprising of methyl 3-chloro propionate, methyl-3-bromo propionate, methyl 3-iodo propionate.

21. The process as claimed in claim 16 wherein the methyl-3-halopropionate is methyl-3-bromo propionate.

22. The process as claimed in claim 16 wherein the solvent is toluene.

23. The process as claimed in claim 16 wherein the temperature is 70° C.

24. A process as claimed in claim 1 which further comprises converting 3-[N-(methylpentyl)amino]propionic acid of formula III to ibandronic acid or its pharmaceutically acceptable salts and hydrates.

* * * * *